United States Patent
Lowery et al.

(10) Patent No.: US 11,752,119 B2
(45) Date of Patent: Sep. 12, 2023

(54) ADMINISTRATION OF BETA-HYDROXYBUTYRATE AND RELATED COMPOUNDS IN HUMANS FOR THE TREATMENT AND/OR PREVENTION OF RESPIRATORY ILLNESSES

(71) Applicant: AXCESS GLOBAL SCIENCES, LLC, Salt Lake City, UT (US)

(72) Inventors: Ryan Lowery, Tampa, FL (US); Jacob Wilson, Tampa, FL (US)

(73) Assignee: AXCESS GLOBAL SCIENCES, LLC, Salt Lake City, UT (US)

( * ) Notice: Subject to any disclaimer, the term of this patent is extended or adjusted under 35 U.S.C. 154(b) by 24 days.

(21) Appl. No.: 17/384,632

(22) Filed: Jul. 23, 2021

(65) Prior Publication Data

US 2022/0023242 A1 Jan. 27, 2022

Related U.S. Application Data

(60) Provisional application No. 63/055,798, filed on Jul. 23, 2020.

(51) Int. Cl.
*A61K 31/19* (2006.01)
*A61P 31/14* (2006.01)
*A61K 9/00* (2006.01)

(52) U.S. Cl.
CPC ............ *A61K 31/19* (2013.01); *A61K 9/0053* (2013.01); *A61P 31/14* (2018.01)

(58) Field of Classification Search
CPC ..................................................... A61K 31/19
See application file for complete search history.

(56) References Cited

U.S. PATENT DOCUMENTS

| | | |
|---|---|---|
| 2006/0280721 A1 | 12/2006 | Veech et al. |
| 2017/0296501 A1 | 10/2017 | Lowery et al. |
| 2020/0129463 A1 | 4/2020 | Lowery et al. |

OTHER PUBLICATIONS

Bradshaw et al., Oxid Med Cell Longev, 2020, 2020: 6401341.*
Kidney Int, 2019, 95(5): 1120-1137(abstract).*
International Preliminary Report on Patentability received for PCT Patent Application No. PCT/US2021/043076, dated Feb. 2, 2023, 8 pages.
International Search Report and Written Opinion received for PCT Patent Application No. PCT/US2021/043076, dated Nov. 9, 2021, 8 pages.
Kaur G. et al., "Sars-Cov-2 Covid-19 Susceptibility and lung Inflammatory Storm by Smoking and Vaping", Journal of Inflammation, Jun. 10, 2020 vol. 17, Article No. 21, pp. 8.

* cited by examiner

*Primary Examiner* — Rei Tsang Shiao
(74) *Attorney, Agent, or Firm* — Workman Nydegger

(57) ABSTRACT

In various implementations, beta-hydroxybutyrate may be orally administered to individuals. Administration may allow treatment and/or prevention of respiratory illnesses, in some implementations. Administration may reduce recovery times and improve outcomes in individuals with respiratory illnesses.

20 Claims, 2 Drawing Sheets

ADMINISTRATION OF BETA-HYDROXYBUTYRATE AND RELATED COMPOUNDS IN HUMANS FOR THE TREATMENT AND/OR PREVENTION OF RESPIRATORY ILLNESSES

CROSS-REFERENCE TO RELATED APPLICATIONS

This application claims the benefit of U.S. Provisional Patent Application No. 63/055,798, entitled "ADMINISTRATION OF BUTYRATE, BETA-HYDROXYBUTYRATE, AND RELATED COMPOUNDS IN HUMANS FOR THE TREATMENT AND/OR PREVENTION OF RESPIRATORY ILLNESSES", filed on Jul. 23, 2020, which is incorporated by reference for all purposes.

TECHNICAL FIELD

The present invention relates to administration of butyrate, beta-hydroxybutyrate, and related compounds for the prevention and/or treatment of illness, specifically respiratory illnesses.

BACKGROUND

Human coronaviruses are common pathogens that induce a variety of illnesses in mammals and humans. Better-known coronaviruses, such as the SARS outbreak in 2002 and the MERS outbreak in 2012, have demonstrated the ability of coronaviruses to cause severe symptoms, including coughing, fever, tiredness, difficulty breathing, inflammation, impaired lung and/or cardiac function and in cases death. Recently, a novel coronavirus (COVID-19) was discovered in humans at the end of 2019 in China. Human-to-human transmission ensued (Li et al. 2020) and the virus quickly became a global pandemic. A compound for the treatment (e.g., cure, inhibition of disease progression, and/or inhibition of disease severity) and/or prevention is needed.

SUMMARY

In various implementations, pharmaceutically effective amount(s) of butyrate, beta-hydroxybutyrate, related compounds, and/or one or more other compounds (e.g., fatty acids or esters thereof, amino acids, AC-11; etc.) may be administered to an individual. For example, the pharmaceutically effective amount(s) of the butyrate, beta-hydroxybutyrate, related compounds, and/or one or more other compounds (e.g., fatty acids or esters thereof, amino acids, AC-11, etc.) may be administered to treat illnesses (e.g., cure, reduce severity of illness or symptom(s) thereof, reduce and/or inhibit disease progression, reduce and/or inhibit symptom(s) of the illness, decrease recovery time, decrease severity of conditions during illness recovery periods, and/or improve mortality) and/or prevent (e.g., reduce the likelihood of infection, increase the likelihood of asymptomatic infection, etc.) illness(es), such as those caused by coronaviruses. The pharmaceutically effective amount of butyrate, beta-hydroxybutyrate, related compounds, and/or one or more other compounds (e.g., fatty acids or esters thereof, amino acids, AC-11, etc.) may be administered to healthy individuals and/or not healthy individuals (e.g., with diseases and/or disorders).

Implementations may include one or more of the following features. The beta-hydroxybutyrate may include the racemic mixture and/or the individual isomers of beta-hydroxybutyrate, such as R-beta-hydroxybutyrate (also known as D-beta-hydroxybutyrate). The beta-hydroxybutyrate may include related compounds. Other compounds may be administered with the beta-hydroxybutyrate such as short chain fatty acids, short chain triglycerides, medium chain fatty acids, medium chain triglycerides, long chain fatty acids, long chain triglycerides, berberine, berberine metabolites, dihydroberberine, tetrahydroberberine, amino acids (e.g., leucine), and/or combinations thereof. In some implementations, medium chain fatty acids (e.g., 6-12 carbon fatty acids) may be administered with beta-hydroxybutyrate. The administered fatty acids and/or triglycerides may be in free form, a natural form (e.g., coconut oil, dairy, and/or palm kernel oil), or derived from a natural form. One or more of the administered compounds may be unencapsulated and/or encapsulated.

In various implementations, the described compound(s) may be administration in a pharmaceutically effective amount to individuals infected with and/or previously infected with a coronavirus.

In various implementations, the described compound(s) may be administered in a pharmaceutically effective amount in healthy individuals to prevent illness (e.g., respiratory illnesses such as coronaviruses) or symptoms thereof, reduce the likelihood of symptomatic illness, and/or increase the likelihood of asymptomatic infection.

In various implementations, the described compound(s) may be administered as a daily supplement (e.g., one or more times a day) to provide described illness (e.g., respiratory illnesses such as coronaviruses) and symptomatic benefits related to infection with coronaviruses and/or to provide one or more other benefits, such as increasing and/or maintaining ketone levels, inducing ketosis, maintaining ketosis, increasing weight loss, maintain weight loss, decrease insulin resistance, increase strength, increase mental acuity, increase metabolism, increase fat loss, increase fat oxidation, increase motor function, increase muscle mass, and/or combinations thereof.

In various implementations, a composition may be orally administered improve respiratory illness(es) in an individual. The composition may include a pharmaceutically effective amount R-beta-hydroxybutyrate. The R-beta-hydroxybutyrate in the composition may include approximately 0.5 g to approximately 10 g of R-beta-hydroxybutyrate. The R-beta-hydroxybutyrate may include at least one R-beta-hydroxybutyrate salt.

Implementations may include one or more of the following features. The composition may include less than approximately 2 g of R-beta-hydroxybutyrate. The approximately R-beta-hydroxybutyrate in the composition may include at least approximately 90% R-beta-hydroxybutyrate and less than approximately 10% L-beta-hydroxybutyrate. The R-beta-hydroxybutyrate of the composition may include at least one a beta-hydroxybutyrate salt and at least one beta-hydroxybutyrate polymer. The R-beta-hydroxybutyrate may include an R-beta-hydroxybutyrate-complex. The composition may include additional compound(s), such as short chain fatty acid(s), ester(s) of short chain fatty acid(s), medium chain fatty acid(s), ester(s) of medium chain fatty acid(s); long chain fatty acid(s), ester(s) of long chain fatty acid(s), and/or combinations thereof. In some implementations, the composition may include approximately 1 g to approximately 20 g of at least one of one or more medium chain fatty acids or one or more medium chain fatty acid esters. The composition in some implementations, may include a C8 fatty acid (e.g., refined, as a fatty acid composition that is enriched in C8, and/or in combination with fatty acids). The composition may include flavoring(s), vitamin(s), mineral(s), and/or liquid carrier(s). The composition may include one or more amino acids. In some implementations, administration of the composition may increase strength and mental acuity in individual(s) with respiratory illness(es). Administration of the composition comprising R-beta-hydroxybutyrate may improve (e.g., reduction of symptoms, reduction in severity, decreased recovery time, etc.) coronavirus respiratory illnesses such as COVID-19. Administration of the composition comprising R-beta-hydroxybutyrate may reduce or long-term symptoms (e.g., symptoms 4 or more weeks after infection) of coronavirus respiratory illnesses such as COVID-19. Administration of the composition comprising R-beta-hydroxybutyrate may the number of symptoms and/or the severity of the symptoms of respiratory illness(es) in individuals.

In various implementations, a composition may be orally administered to improve lung function in an individual with a respiratory illness. The composition may include a pharmaceutically effective amount beta-hydroxybutyrate. The beta-hydroxybutyrate in the composition may include approximately 0.5 g to approximately 10 g of beta-hydroxybutyrate. The beta-hydroxybutyrate may include at least one beta-hydroxybutyrate salt.

Implementations may include one or more of the following features. The administration of the composition may improve lung function in an individual with at least one respiratory illness. The administration of the composition may improve lung function due to reduced lung function from viral respiratory illness(es), such as coronavirus illnesses. The administration of the composition may improve lung function due to reduced lung function from bacterial or fungi respiratory illness(es). In some implementations, the composition may include less than approximately 2 g of beta-hydroxybutyrate. The beta-hydroxybutyrate in the composition may include at least approximately 90% R-beta-hydroxybutyrate and less than approximately 10% L-beta-hydroxybutyrate.

In various implementations, a composition may be orally administered to improve respiratory illnesses in an individual with a respiratory illness. The composition may include a pharmaceutically effective amount beta-hydroxybutyrate. The beta-hydroxybutyrate in the composition may include approximately 0.5 g to approximately 10 g of beta-hydroxybutyrate. The beta-hydroxybutyrate may include at least one beta-hydroxybutyrate salt.

Implementations may include one or more of the following features. The administration of the composition may improve the respiratory illness in the individual. The composition may include at least one beta-hydroxybutyrate polymer. The composition may further include at least one amino acid.

The details of one or more implementations are set forth in the accompanying drawings and the description below. Other features, objects, and advantages of the implementations will be apparent from the description and drawings.

BRIEF DESCRIPTION OF THE DRAWINGS

For a more complete understanding of this disclosure and its features, reference is now made to the following description, taken in conjunction with the accompanying drawings, in which.

Like reference symbols in the various drawings indicate like elements.

DETAILED DESCRIPTION

Figure 1:
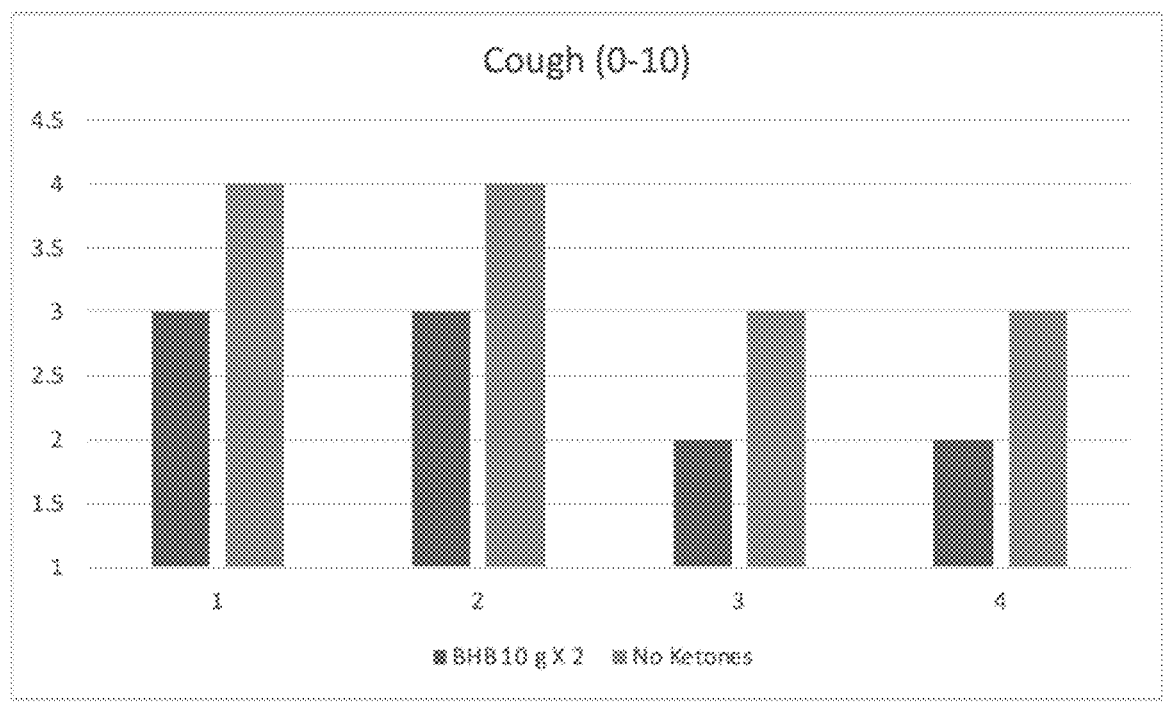
FIG. 1 illustrates a chart of cough severity over time for an implementation of an example administration of beta-hydroxybutyrate in individuals with respiratory illnesses.

In various implementations, compounds such as butyrate, beta-hydroxybutyrate, and/or related compounds (e.g., derivatives, esters, complexes, polymers, etc.) can be administered alone or in combination with one or more other compounds, such as fatty acids; and, the administration of a pharmaceutically effective amount of these compound(s) may prevent and/or treat respiratory illnesses such as illnesses caused by coronaviruses (e.g., SARS, MERS, COVID-19, and/or mutations thereof). In some implementations, blood ketone levels and/or blood glucose levels may be reduced and/or maintained within a predetermined range when a pharmaceutically effective amount of one or more compounds are administered. In some implementations, a health of an individual (e.g., strength, symptoms of disease, mental acuity, fasting glucose levels, etc.) may be improved and/or maintained by administration of a compound that includes butyrate, beta-hydroxybutyrate, and/or related compounds (e.g., derivatives, esters, polymers, etc.), and/or other compounds.

In various implementations, compounds may include butyrate, beta-hydroxybutyrate, related compounds (e.g., derivatives, esters, complexes, polymers, etc.), fatty acids, and/or esters of fatty acids can be administered alone or in combination with one or more other compounds (e.g., amino acids, AC-11); and, the administration of a pharmaceutically effective amount of these compound(s) may prevent and/or treat respiratory illnesses such as illnesses caused by coronaviruses (e.g., SARS, MERS, COVID-19, and/or mutations thereof). In some implementations, blood ketone levels and/or blood glucose levels may be reduced and/or maintained within a predetermined range when a pharmaceutically effective amount of one or more compounds are administered. In some implementations, a health of an individual (e.g., strength, symptoms of disease, mental acuity, fasting glucose levels, etc.) may be improved and/or maintained by administration of the compound.

In various implementations, a composition administered for the prevention and/or treatment of respiratory illnesses and/or symptoms thereof may include butyrate, beta-hydroxybutyrate, and/or fatty acids or esters thereof. The respiratory illnesses may pathogenic (e.g., caused by virus, bacteria, etc.). In some implementations, other additional compounds may be included in the administered compound. The composition may be administered with other known treatments for the respiratory disease (e.g., steroids, antibiotics, antivirals, etc.). The addition of the administration of the described composition(s) to the known treatments may decrease symptom severity, decrease the severity of the course of the respiratory illness, and/or reduce recovery time.

In various implementations, the beta-hydroxybutyrate in the described composition may include racemic (e.g., D,L-beta-hydroxybutyrate) or non-racemic mixtures of R-beta-hydroxybutyrate and L-beta-hydroxybutyrate. Non-racemic mixtures may or may not include 100% of a selected isomer. For example, R-beta-hydroxybutyrate may include approximately 90 to approximately 100% of R-beta-hydroxybutyrate and approximately 0 to approximately 10% of L-beta-hydroxybutyrate. As described in U.S. patent application Ser. No. 15/491,924, the specific chirality selected or included in a higher amount may be based on desired range of bioavailability and/or desired health improvements such as increasing ketone levels, weight loss, mental acuity, fat loss, strength, etc. In some implementations, a naturally synthesized form of a beta-hydroxybutyrate isomer, such as R-beta-hydroxybutyrate (commercially available in Keto-Nat from Pruvit, Melissa Tx.) may be utilized. The naturally synthesized form of R-beta hydroxybutyrate may increase user satisfaction with a compound due to its natural origin and/or reduced impurities due to manufacturing (e.g., less crotonic acid, which can be harmful to individuals).

Beta-hydroxybutyrate may include beta-hydroxybutyrate salts and/or beta-hydroxybutyrate esters. In some implementations, beta-hydroxybutyrate may include beta-hydroxybutyrate bound to another compound (e.g., amino acids) and/or polymers of beta-hydroxybutyrate. For example, beta-hydroxybutyrate (e.g., R-beta-hydroxybutyrate, L-beta-hydroxybutyrate, and/or D,L-beta-hydroxybutyrate) may include beta-hydroxybutyrate salts, beta-hydroxybutyrate esters, beta-hydroxybutyrate sodium salt (e.g., sodium beta-hydroxybutyrate), beta-hydroxy butyrate potassium salt (e.g., potassium beta-hydroxybutyrate), beta-hydroxybutyrate calcium salt (e.g., calcium beta-hydroxybutyrate), beta-hydroxybutyrate magnesium salt (e.g., magnesium beta-hydroxybutyrate), beta-hydroxybutyrate lithium salt (e.g., lithium beta-hydroxybutyrate), sodium beta-hydroxybutyrate, arginine beta-hydroxybutyrate, lysine beta-hydroxybutyrate, histidine beta-hydroxybutyrate, ornithine beta-hydroxybutyrate, creatine beta-hydroxybutyrate, agmatine beta-hydroxybutyrate, or citrulline beta-hydroxybutyrate, other appropriate organic salts that include beta-hydroxybutyrate, and/or combinations thereof.

In some implementations, the beta-hydroxybutyrate may include one or more beta-hydroxybutyrate salts that include calcium, sodium, magnesium, potassium, zinc, selenium, chromium, or other appropriate minerals. For example, the beta-hydroxybutyrate (e.g., R-beta-hydroxybutyrate, L-beta-hydroxybutyrate, and/or D,L-beta-hydroxybutyrate) may include beta-hydroxybutyrate sodium salt (e.g., sodium beta-hydroxybutyrate), beta-hydroxy butyrate potassium salt (e.g., potassium beta-hydroxybutyrate), beta-hydroxybutyrate calcium salt (e.g., calcium beta-hydroxybutyrate), and/or beta-hydroxybutyrate magnesium salt (e.g., magnesium beta-hydroxybutyrate). The selection and/or ratio of types of beta-hydroxybutyrate salt may promote replenishment of depleted minerals (e.g., due to illness).

In some implementations, the beta-hydroxybutyrate may be complexed and/or coupled to another compound (e.g., amino acid and/or berberine) and a beta-hydroxybutyrate salt may include a complex (e.g., chelate) that includes a mineral (e.g., calcium, zinc, etc.) and the beta-hydroxybutyrate compound coupled to another compound. The beta-hydroxybutyrate may include single isomer beta-hydroxybutyrate and/or polymer beta-hydroxybutyrate. For example, beta-hydroxybutyrate may include single isomer beta-hydroxybutyrate and polymer beta-hydroxybutyrate. As another nonlimiting example, beta-hydroxybutyrate may include beta-hydroxybutyrate salt and polymer R-beta-hydroxybutyrate. In some implementations, beta-hydroxybutyrate may be administered with 1,3-butanediol, ethyl acetoacetate, and/or ethyl beta-hydroxybutyrate.

In some implementations, the beta-hydroxybutyrate composition may include beta-hydroxybutyrate salt and beta-hydroxybutyrate esters. For example, an individual may be administered a first weight amount of sodium beta-hydroxybutyrate and a second weight amount of beta-hydroxybutyrate ester. The first amount and the second amount may be different or the same. The beta-hydroxybutyrate salt and the beta-hydroxybutyrate ester may be a bound complex, a mixture of compounds, and/or separately administered approximately concurrently. In some implementations, the beta-hydroxybutyrate ester may be in powdered form (e.g., plated beta-hydroxybutyrate ester), liquid and/or gel form. The combination of beta-hydroxybutyrate salt and beta-hydroxybutyrate ester during administration may allow less salt to be utilized while producing a result (e.g., weight maintenance and/or loss; enhanced and/or maintained ketosis; elevated blood ketone levels; blood glucose reduction and/or maintenance; increase in energy; increase in mood; increase in performance; and/or increase in cognitive function). In some implementations, elevated ketone levels (e.g., elevated blood ketone levels) may increase energy, mood, performance, and/or cognitive function in users. For example, the administration of the first amount of beta-hydroxybutyrate salt may cause a first level of blood ketone level, which may be maintained by processing of the second amount of the beta-hydroxybutyrate ester (e.g., as the body of the individual processes the beta-hydroxybutyrate ester the level of beta-hydroxybutyrate in the blood, and thus blood ketone level, may also increase over time to enhance and/or maintain the initial elevation caused by of the administered beta-hydroxybutyrate salt.). For example, a ratio of beta-hydroxybutyrate to beta-hydroxybutyrate ester may be approximately 1 beta-hydroxybutyrate salt: approximately 1 beta-hydroxybutyrate ester to approximately 1 beta-hydroxybutyrate salt: approximately 20 beta-hydroxybutyrate ester. The ratio of beta-hydroxybutyrate to beta-hydroxybutyrate ester may be approximately 20 beta-hydroxybutyrate salt: approximately 1 beta-hydroxybutyrate ester to approximately 1 beta-hydroxybutyrate salt: approximately 20 beta-hydroxybutyrate ester. In some implementations, a ratio of beta-hydroxybutyrate to beta-hydroxybutyrate ester may be approximately 1 beta-hydroxybutyrate salt: approximately 1 beta-hydroxybutyrate ester to approximately 1 beta-hydroxybutyrate salt: approximately 5 beta-hydroxybutyrate ester.

Related compounds that may be included as beta-hydroxybutyrate in the composition may include derivatives of beta-hydroxybutyrate, include esters of (R)-3-hydroxybutyrate and oligomers of (R)-3-hydroxybutyrate. For example, beta-hydroxybutyrate esters derived from alcohols, such as altrose, arabinose, dextrose, erythrose, fructose, galactose, glucose, glycerol, glucose, idose, lactose, lyxose, mannose, ribitol, ribose, ribulose, sucrose, talose, threose, xylitol, xylose, galactosamine, glucosamine, mannosamine, N-acetylglucosamine, mannitol, sorbitol, threitol, (S)-1,2-propanediol and/or (R)-1,3-butanediol. In some implementations, a derivative of the beta-hydroxybutyrate may include structures of (R)-3-hydroxybutyric acid and an exemplary ester thereof (a glycerol monoester). The R chirality of the derivatives may be selected for inclusion in the composition in some implementations (e.g., to deliver R-beta-hydroxybutyrate with the administration of the compound).

In various implementations, the described compound may include one or more fatty acids and/or esters thereof (e.g., triglyceride). For example, the described compound may include short chain fatty acids (e.g., fatty acid with between 2 carbons than 6 carbons), short chain triglycerides (e.g., triglycerides with less than 6 carbons such as butyric acid and/or butyrate), medium chain fatty acids (e.g., fatty acid with 6-12 carbons), medium chain triglycerides (e.g., triglycerides with 7-12 carbons), long chain fatty acids (e.g., fatty acids with more than 12 carbons), long chain triglycerides (e.g., triglycerides with more than 12 carbons), and/or combinations thereof.

In some implementations, approximately 1 g to approximately 15 g of beta-hydroxybutyrate and approximately 0.1 g to approximately 50 g of short chain fatty acid and/or triglyceride may be administered from once a day to approximately 5 times a day. In some implementations, the short chain fatty acid and/or triglyceride may include butyrate or derivatives of butyrate. Butyrate and/or derivatives of butyrate may be administered with and/or without beta-hydroxybutyrate to manage metabolic conditions, such as ketosis, and/or for other appropriate therapeutic purposes. Administered butyrate may be converted to beta-hydroxybutyrate in humans, and thus may increase the amount of beta-hydroxybutyrate delivered to the user. Since butyrate is processed by the body to provide beta-hydroxybutyrate, the delivery of beta-hydroxybutyrate via the butyrate may supplement the directly administered beta-hydroxybutyrate to maintain a level of beta-hydroxybutyrate in the blood (e.g., to promote ketosis, weight loss and/or management, etc.).

In some implementations, a C8 fatty acid or ester thereof may be included in the administered compound. In some implementations, a custom blend of fatty acids with a high percentage of C8 fatty acid (e.g., greater than approximately 50%) and/or refined C8 fatty acid may be utilized. In some implementations, short chain fatty acids and/or triglycerides may include acetate, propionate, and/or butyrate. Medium chain fatty acids and/or triglycerides may include lauric acid and/or coconut oil, coconut milk powder, fractionated coconut oil, isolated hexanoic acid, isolated octanoic acid, isolated decanoic acid, ethoxylated triglyceride, triglyceride derivatives thereof, aldehyde triglyceride derivatives thereof, monoglyceride derivatives thereof, diglyceride derivatives thereof, triglyceride derivatives thereof, and/or alkyl esters thereof. Long chain fatty acids and/or triglycerides may include dairy products and/or palm oil. The administered fatty acids and/or triglycerides may be in free form, a natural form (e.g., coconut oil, dairy, and/or palm kernel oil), or derived from a natural form. One or more of the administered compounds may be unencapsulated and/or encapsulated.

In some implementations, a pharmaceutically effective amount of one or more short chain fatty acids and/or one or more short chain triglycerides (e.g., butyric acid and/or butyrate) may be administered with a pharmaceutically effective amount of beta-hydroxybutyrate. In some implementations, the short chain fatty acid and/or triglyceride may include butyrate or derivatives of butyrate. In some implementations, a pharmaceutically effective amount of one or more medium chain fatty acids and/or one or more medium chain triglycerides (e.g., butyric acid and/or butyrate) may be administered with a pharmaceutically effective amount of beta-hydroxybutyrate. In some implementations, a pharmaceutically effective amount of one or more long chain fatty acids and/or one or more long chain triglycerides (e.g., butyric acid and/or butyrate) may be administered with a pharmaceutically effective amount of beta-hydroxybutyrate. In some implementations, the described compound may include a mixture of fatty acids or esters thereof and beta-hydroxybutyrate (e.g., one or more beta-hydroxybutyrate salts) in pharmaceutically effective amounts. The mixture of fatty acids or esters may be naturally sourced and/or derived from natural sources, in some implementations.

In various implementations, the described compound may include approximately 0.5 to approximately 15 g of beta-hydroxybutyrate compound and approximately 1 g to approximately 20 g of another compound such as a medium chain fatty acid or ester thereof (e.g., triglyceride). In some implementations, the compound administered may include approximately 5 to approximately 10 g of beta-hydroxybutyrate compound and approximately 10 to approximately 20 g of medium chain fatty acid or ester thereof (e.g., triglyceride). In some implementations, the compound administered may include approximately 6 to approximately 8 g of beta-hydroxybutyrate compound and approximately 1 g to 20 g of medium chain fatty acid or ester thereof (e.g., triglyceride). The combination of the beta-hydroxybutyrate and medium chain fatty acid or ester thereof may provide an improvement in the health of an individual (e.g., reduced illness time, decreased severity of disease, improved recovery period, etc.) that is not seen or with administration of either portion separately. In addition, the ability a compound including beta-hydroxybutyrate and medium chain to improve outcomes, recovery periods, or impact respiratory health is unexpected.

In some implementations, the described compound may include one or more additional compounds such as an amino acid and/or amino acid metabolites. For example, beta-hydroxybutyrate of the described compound may be administered with and/or coupled to (e.g., chemically bonded to) amino acids, such as leucine, lysine, arginine, histidine, ornithine, creatine, agmatine, citrulline and/or combinations thereof. In some implementations, R-beta-hydroxybutyrate may be utilized rather than other chiralities since R-beta-hydroxybutyrate may be more easily bound to leucine, purine, lysine, and/or other amino acids. Administration of beta-hydroxybutyrate that is coupled to an amino acid may reduce the intake of cations associated with beta-hydroxybutyrate salt administration (e.g., which may inhibit side effects associated with administration) and/or allow administration of another compound that has health benefits (e.g., administration of some amino acid may promote smooth muscle growth and/or cell repair). In some implementations, approximately 0.5 g to approximately 10 g of amino acid may be included in the administered compound. For example, approximately 0.5 to approximately 15 g of beta-hydroxybutyrate and less than approximately 60 mg of an amino acid, such as leucine, may be administered daily. In some implementations, approximately 0.5 g to approximately 2 g of an amino acid, such as leucine, may be administered with a beta-hydroxybutyrate. For example, approximately the composition administered may include approximately 0.1 to approximately 7 g R-beta-hydroxybutyrate and approximately 1-3 g of leucine. The leucine may be included in the compound; administered separately and proximate in timing; a complex; and/or administered in any other appropriate manner.

In some implementations, the composition may include a beta-hydroxybutyrate salt and beta-hydroxybutyrate-amino acid complex (e.g., beta-hydroxybutyrate bound to amino acid, such as R-beta-hydroxybutyrate-leucine complex). For example, an individual may be administered a first weight amount of sodium beta-hydroxybutyrate and a second weight amount of beta-hydroxybutyrate amino-acid complex. The first amount and the second amount may be different or the same.

In some implementations, the described compound may include additional compounds such as a pharmaceutically effective amount of butyrate administered via triglyceride tributyrin (e.g., glyceryl tributyrate or tributyrin). For example, up to approximately 200 mg/kg of the butyrate administered via triglyceride tributyrin may be administered (e.g., up to 3 times daily). Administration of the tributyrin may allow a delayed release of butyrate to the body as the tributyrin is processed by the body of the individual. The tributyrin may be unencapsulated and/or encapsulated (e.g., microencapsulated).

In some implementations, the described compound may include one or more additional compounds such as compounds capable of independently decreasing glucose levels such as berberine and/or associated metabolites (e.g., dihydroberberine and/or tetrahydroberberine). U.S. patent application Ser. No. 15/491,933 entitled "ADMINISTRATION OF DIHYDROBERBERINE" to Lowery et al, filed Apr. 19, 2017 and U.S. Provisional Patent Application No. 62/324,794, entitled "ADMINISTRATION OF DIHYDROBERBERINE" to Lowery et al, filed Apr. 19, 2016, describe dihydroberberine administration with ketone sensitizers such as beta-hydroxybutyrate, and is hereby fully incorporated herein. In some implementations, one or more beta-hydroxybutyrates and/or other compounds described herein may be utilized as a ketone sensitizer with the dihydroberberine.

In some implementations, directly administering beta-hydroxybutyrate plus another compound that is processed to deliver beta-hydroxybutyrate (e.g., beta-hydroxybutyrate ester, beta-hydroxybutyrate polymer, butyrate, other appropriate compounds, and/or combinations thereof) over time may allow a first level of beta-hydroxybutyrate in the blood to be maintained over a period of time. For example, since the directly administered beta-hydroxybutyrate may elevate blood beta-hydroxybutyrate levels to a first concentration and this concentration may be approximately maintained over a period of time by providing additional beta-hydroxybutyrate via another compound administered approximately concurrently (e.g., short chain fatty acid and/or triglyceride, beta-hydroxybutyrate ester, beta-hydroxybutyrate polymer, beta-hydroxybutyrate amino acid complex, etc.).

In some implementations, one or more other compounds may be administered with and/or included in the described composition including, but not limited to, vitamins, minerals, coconut milk powder, AC-11, flavorings, colorings, binders, electrolytes, tetrahydrobiopterin, nucleic acids, alpha-ketoglutaric acid, alpha lipoic acid, nutritional co-factors, beta-methyl-beta-hydroxybutyrate, arginine alpha-ketoglutarate, R-alpha lipoic acid, thiamine, NAD+, NADH, riboflavin, FAD+, FADH, riboflavin-5-phosphate, niacin, nicotinic acid, niacinamide, inositol hexanicotinate, pyridoxine, pyridoxal, pyridoxamine, ascorbic acid and ascorbate salts, citric acid, malic acid, sodium benzoate, Pyridoxal-5-Phosphate, methylcobalamin, cyanocobalamin, adenosyl cobalamin, hydroxycobalamin, pantothenic acid, pantetheine, potassium sorbate, acesulfame K, aspartame, sucralose, stevia, monk fruit extract, allulose, prebiotic fibers, XOS, GOS, MOS, IMO, LOS, xanthan gum and other organic gums/thickeners/suspension agents, and combinations thereof.

In various implementations, the compound administered may include approximately 0.5 to approximately 15 g of beta-hydroxybutyrate compound and approximately 1 g to approximately 20 g of another compound such as a medium chain fatty acid or ester thereof (e.g., triglyceride). In some implementations, the compound administered may include approximately 5 to approximately 10 g of beta-hydroxybutyrate compound and approximately 10 to approximately 20 g of medium chain fatty acid or ester thereof (e.g., triglyceride). In some implementations, the compound administered may include approximately 6 to approximately 8 g of beta-hydroxybutyrate compound and approximately 1 g to 20 g of medium chain fatty acid or ester thereof (e.g., triglyceride).

In various implementations, the described compound may be administered in healthy and not healthy individuals (e.g., individuals with diseases and/or disorders).

The administration of a pharmaceutically effective amount may be utilized to treat individuals with respiratory illnesses, such as respiratory illnesses caused by coronaviruses, reduce symptoms from respiratory illnesses, reduce disease progression, reduce disease severity, reduce probability of morbidity, reduce other present diseases or symptoms thereof to reduce morbidity rates due to comorbidity, and/or combinations thereof. The administration of the described compound may decrease cough, fever, tiredness, difficulty breathing, inflammation, and/or impaired lung function. The administration of the compound may improve health in respiratory illnesses, such as those caused by coronaviruses. Administration of the described compound may reduce inflammation to inhibit cytokine release syndrome and/or reduce damaging inflammation to the lungs and/or heart. Reduction in probability of cytokine release syndrome occurrence may reduce the chance of death and/or decrease the length of illness and/or hospital stays. The reduction in inflammation of lungs and/or hearts in individuals due to the administration of the described compound may decrease long term health problems associated with recovering and recovered coronavirus (e.g., decrease need for transplants, long term oxygen use, etc.). Administration of the described compound in patients with respiratory illnesses may also increase user health which results in decrease recovery time and/or hospital stays. For example, administration of the described compound may reduce the decrease in physical strength and muscle mass which is common during the reduced activity periods associated with respiratory illnesses. As another nonlimiting example, the administration of the compound may improve health related to other comorbidity factors such as obesity and diabetes. The composition may include 0.5 to 10 g of beta-hydroxybutyrate. The beta-hydroxybutyrate may be R-betahydroxybutyrate. The beta-hydroxybutyrate may comprise one or more beta-hydroxybutyrate salts. The compound may include one or more additional compounds. For example, the composition administered may include approximately 0.5 to approximately 15 g of beta-hydroxybutyrate compound and approximately 1 g to approximately 20 g of medium chain fatty acid or ester thereof (e.g., triglyceride).

In various implementations, the administration of a pharmaceutically effective amount may be used to improve user health during recovery periods after respiratory illnesses, such as respiratory illnesses caused by coronaviruses (e.g., when compared with conventional therapies). Recovery from respiratory illnesses may be associated with long recovery periods (e.g., when an individual tests negative after previous positive coronavirus tests) and may be in which individuals feel mental fog and fatigue (e.g., symptoms 4 or more weeks after infection). The administration of the composition comprising beta-hydroxybutyrate may decrease the recovery time, decrease symptoms during the long recovery period, and/or increase endurance (e.g., while decreased from normal during long term recovery, administration of the composition may increase the endurance when compared to individuals who are not administered the composition). In some implementations, administration of the described compound may improve muscle mass which may reduce recovery periods (e.g., associated with regaining strength). Administration of the described compound may improve health by improving mental clarity, improving endurance, increasing strength, and decreasing inflammation found in the body after prolonged illness. Improving health during recovery by administering the described compound may reduce the length of recovery (e.g., to when an individual feels normal again) and improve an individual's mental health.

In various implementations, the administration of a pharmaceutically effective amount may be used to improve lung function in individuals with respiratory illnesses (e.g., pathogenic respiratory illnesses). Reduction of lung function may lower during illness and/or recovery periods when the composition is administered. The length of time that substantial reduction of lung function presents in an individual with respiratory illnesses may decrease when the composition is administered.

The administration of a pharmaceutically effective amount may be used to prevent respiratory illnesses, such as respiratory illnesses caused by coronaviruses, in individuals and/or to increase the likelihood of asymptomatic respiratory illnesses. Administration may reduce inflammation. Since general persistent inflammation may decrease the ability of an individual to fight viruses, the administration of the described compound may reduce the likelihood of infection and/or increase the change of asymptomatic infection (e.g., since general health may be increased).

The administration may also cause when used as a supplement in healthy people and/or asymptomatically ill people, weight loss and/or maintenance; elevated beta-hydroxybutyrate levels in the blood; elevated, reduced, and/or maintenance of blood ketone levels; induction and/or maintenance of ketosis; and/or reduction; improved mental acuity; improved focus; improved energy; improved cognitive function; improved diabetes; improved glucose tolerance; decreased blood glucose levels; reduced neurological disorders and/or symptoms thereof; improve inflammatory conditions; decrease in inflammation in the body; suppressing appetite; improve symptoms associated with aging; provide anti-glycation affects; improve epilepsy and/or symptoms thereof; improve depression and/or symptoms thereof; improve performance; improve strength; increase muscle mass; increase fat loss; improve body composition; improve energy; improve focus; improve cognitive function; improve mood and/or well-being; and/or combinations thereof.

In some implementations, administration of the described compound may improve, maintain, and/or decrease the decline in respiratory function associated with respiratory illnesses.

In some implementations, administration of described compound may increase mental acuity, increase muscle protein synthesis, performance and decrease perceived exertion, improve and/or maintain health markers such as C-reactive protein and/or fasting glucose, improve motor function, improve and/or maintain cognitive function. Administration of the described compound may increase fat loss, which may improve health and the ability of the body to continue to fight severe disease progressions. Unlike with conventional diets, in which weight loss often comes from decreases in water retention and/or muscle mass, administration of R-beta-hydroxybutyrate may cause decreases in fat loss.

Administration of the described compound may decrease inflammation (e.g., as shown by C-reactive protein levels).

In some implementations, the amount of composition administered and the formula of the compound administered may be selected to obtain a result (e.g., reduce comorbidity factors, decrease inflammation, increase glucose tolerance, increase mineral replenishment, induce ketosis; maintain ketosis; increase ketone levels, mental acuity, strength, etc.). The pharmaceutically effective amount may be administered at a dosage and/or over a predetermined time period, in various implementations. In some implementations, the dosage and/or frequency of dosage may vary over time (e.g., initial vs a lower dosage for maintenance, vary based on time of day, vary based on whether taken with or without a meal, based on illness being treated, based on whether the individual is asymptomatic, based on whether the individual is in a recovery period, etc.).

The composition may be administered in any appropriate delivery form (e.g., tablet; capsule; food products such as powdered products that can be mixed into food, mixed into beverages, and/or consumed directly; beverage product; etc.). The composition may be administered according to any appropriate schedule (e.g., periodic dosages, dosages as user desires, etc.). The administration schedule may inhibit administration that elevates blood ketone levels too high, decreases blood glucose levels too low, and/or causes an individual to consume a dosage that substantially elevates the risk of adverse and/or side effects, in some implementations.

In some implementations, the composition may include a long acting component and/or be long-acting. For example, since the body digests polymers and/or esters of beta-hydroxybutyrate (e.g., R-beta-hydroxybutyrate), the delivery of R-beta-hydroxybutyrate may be slower than a digestion of a beta-hydroxybutyrate salt (e.g., R-beta-hydroxybutyrate salt). In some implementations, the composition may include a R-beta-hydroxybutyrate salt and a long acting R-beta-hydroxybutyrate form (e.g., polymer, ester, coated and/or processed form to provide slow release). In some implementations, a first dose(s) may include at least one non-long acting form of beta-hydroxybutyrate and a second dose(s) may include at least one long-acting form of beta-hydroxybutyrate. The first dose(s) may be administered to cause a predetermined health impact and the second dose(s) may be administered to maintain the caused predetermined health impact. In some implementations, users may select the appropriate dose based on user preference and/or properties (e.g., a user on a ketogenic diet may chose the second dose since the user may already be in ketosis). In some implementations, physicians may select the appropriate dose based on user illness severity and/or risk factors for illness.

In various implementations, the compound may including approximately 0.5 g to approximately 15 g of beta-hydroxybutyrate and approximately 1 g to approximately 20 g of fatty acid or ester thereof. The compound may be administered orally 1 to 5 times a day. The compound may be administrable in patients with positive coronavirus test results and/or suspected coronavirus illnesses to maintain health, improve health, reduce a severity of the disease, and/or reduce the severity of symptoms of a disease. The compound may be administrable in patients recovering from coronavirus and/or suspected coronavirus illnesses to maintain health, improve health, reduce a recovery time, and/or reduce symptoms during recovery. The compound may be administrable in patients that were asymptomatic (e.g., with positive coronavirus test results) and/or healthy individuals (e.g., with negative suspected coronavirus illness test results) to maintain health, improve health, reduce a severity of the disease, and/or reduce the severity of symptoms of a disease.

In various implementations, the compound may including approximately 0.5 g to approximately 15 g of beta-hydroxybutyrate. The compound may be administered orally 1 to 5 times a day. The compound may be administrable in patients with positive coronavirus test results and/or suspected coronavirus illnesses to maintain health, improve health, reduce a severity of the disease, and/or reduce the severity of symptoms of a disease. The compound may be administrable in patients recovering from coronavirus and/or suspected coronavirus illnesses to maintain health, improve health, reduce a recovery time, and/or reduce symptoms during recovery. The compound may be administrable in patients that were asymptomatic (e.g., with positive coronavirus test results) and/or healthy individuals (e.g., with negative suspected coronavirus illness test results) to maintain health, improve health, reduce a severity of the disease, and/or reduce the severity of symptoms of a disease.

In various implementations, the compound may including approximately 0.5 g to approximately 10 g of beta-hydroxybutyrate. The beta-hydroxybutyrate in the composition may be one or more salts of beta-hydroxybutyrate. In some implementations, a polymer of beta-hydroxybutyrate may be included in the composition. The composition may be administered orally 1 to 5 times a day. The compound may be administrable in patients with positive coronavirus test results and/or suspected coronavirus illnesses to maintain health, improve health, reduce a severity of the disease, and/or reduce the severity of symptoms of a disease. The compound may be administrable in patients recovering from coronavirus and/or suspected coronavirus illnesses to maintain health, improve health, reduce a recovery time, and/or reduce symptoms during recovery. The compound may be administrable in patients that were asymptomatic (e.g., with positive coronavirus test results) and/or healthy individuals (e.g., with negative suspected coronavirus illness test results) to maintain health, improve health, reduce a severity of the disease, and/or reduce the severity of symptoms of a disease.

In various implementations, the compound may including approximately 1 g to approximately 20 g of medium chain fatty acid. The compound may be administered orally 1 to 5 times a day. The compound may be administrable in patients with positive coronavirus test results and/or suspected coronavirus illnesses to maintain health, improve health, reduce a severity of the disease, and/or reduce the severity of symptoms of a disease. The compound may be administrable in patients recovering from coronavirus and/or suspected coronavirus illnesses to maintain health, improve health, reduce a recovery time, and/or reduce symptoms during recovery. The compound may be administrable in patients that were asymptomatic (e.g., with positive coronavirus test results) and/or healthy individuals (e.g., with negative suspected coronavirus illness test results) to maintain health, improve health, reduce a severity of the disease, and/or reduce the severity of symptoms of a disease.

In various implementations, the compound may including approximately 0.5 g to approximately 15 g of beta-hydroxybutyrate and approximately 1 g to approximately 20 g of medium chain fatty acid. The compound may be administered orally 1 to 5 times a day. The compound may be administrable in patients with positive coronavirus test results and/or suspected coronavirus illnesses to maintain health, improve health, reduce a severity of the disease, and/or reduce the severity of symptoms of a disease. The compound may be administrable in patients recovering from coronavirus and/or suspected coronavirus illnesses to maintain health, improve health, reduce a recovery time, and/or reduce symptoms during recovery. The compound may be administrable in patients that were asymptomatic (e.g., with positive coronavirus test results) and/or healthy individuals (e.g., with negative suspected coronavirus illness test results) to maintain health, improve health, reduce a severity of the disease, and/or reduce the severity of symptoms of a disease.

In various implementations, the compound may including approximately 0.5 g to approximately 15 g of beta-hydroxybutyrate and one or more amino acids. The composition may include leucine. The composition may include approximately 0.5 to approximately 2 g of one or more amino acids. The composition may include approximately 0.5 g to approximately 10 g of amino acid to be administered with the beta-hydroxybutyrate. The compound may be administered orally 1 to 5 times a day. The compound may be administrable in patients with positive coronavirus test results and/or suspected coronavirus illnesses to maintain health, improve health, reduce a severity of the disease, and/or reduce the severity of symptoms of a disease. The compound may be administrable in patients recovering from coronavirus and/or suspected coronavirus illnesses to maintain health, improve health, reduce a recovery time, and/or reduce symptoms during recovery. The compound may be administrable in patients that were asymptomatic (e.g., with positive coronavirus test results) and/or healthy individuals (e.g., with negative suspected coronavirus illness test results) to maintain health, improve health, reduce a severity of the disease, and/or reduce the severity of symptoms of a disease.

In various implementations, the compound may including approximately 0.5 g to approximately 15 g of beta-hydroxybutyrate and leucine. The composition may include approximately 1 to approximately 3 g of one or more amino acids. The composition may include approximately 0.5 g to approximately 10 g of amino acid to be administered with the beta-hydroxybutyrate. The compound may be administered orally 1 to 5 times a day. The compound may be administrable in patients with positive coronavirus test results and/or suspected coronavirus illnesses to maintain health, improve health, reduce a severity of the disease, and/or reduce the severity of symptoms of a disease. The compound may be administrable in patients recovering from coronavirus and/or suspected coronavirus illnesses to maintain health, improve health, reduce a recovery time, and/or reduce symptoms during recovery. The compound may be administrable in patients that were asymptomatic (e.g., with positive coronavirus test results) and/or healthy individuals (e.g., with negative suspected coronavirus illness test results) to maintain health, improve health, reduce a severity of the disease, and/or reduce the severity of symptoms of a disease.

In some implementations, the composition including beta-hydroxybutyrate may be utilized in individuals with coronavirus respiratory illnesses. The individuals may have decreased symptoms (e.g., number and/or severity), decreased illness severity, decreased likelihood of long-term symptoms, and/or shorter recovery times. In individuals that develop long-term symptoms, the administration of the composition may increase alertness, focus, and/or endurance which may make long term symptoms more tolerable than without administration of the compound (e.g., such that individuals may return to daily life).

EXAMPLES

Example 1

A set of compounds including approximately 0.5 g to approximately 15 g of beta-hydroxybutyrate and approximately 1 g to approximately 20 g of medium chain fatty acid was produced for administration.

Example 2

The compound is administrable in patients with positive coronavirus test results and/or suspected coronavirus illnesses to improve health.

Example 3

The compound is administrable in patients with in recovering from coronavirus and/or suspected coronavirus illnesses to improve health.

Example 4

The compound is administrable in patients that were asymptomatic (e.g., with positive coronavirus test results) and/or healthy individuals (e.g., with negative suspected coronavirus illness test results) to improve health.

Example 5

A composition comprising 10 g of R-beta-hydroxybutyrate was administered to individuals twice a day. The individuals had a respiratory illness, COVID-19. The patients were tested and monitored to determine the impact of administration of beta-hydroxybutyrate on the illness progression and recovery. Administration of the beta-hydroxybutyrate reduced the number of symptoms and the severity of symptoms. Administration of the beta-hydroxybutyrate also decreased the recovery time. Since quicker returns to normal values may indicate less chances for long-term continuance of viral respiratory illnesses (e.g., long-haul or long-term covid), administration of beta-hydroxybutyrate may be associated with decreased potential for long-term continuance of symptoms.

FIG. 1 illustrates cough measured over 4 days for individuals administrated 10 g of R-beta-hydroxybutyrate and not administered 10 g of R-beta-hydroxybutyrate. Cough severity was measured using the Cough Severity Visual Analogue Scale. As illustrated, cough severity was lower with administration of 10 g of R-beta-hydroxybutyrate. Furthermore, cough severity was not as high when beta-hydroxybutyrate was orally administered.

Figure 2:
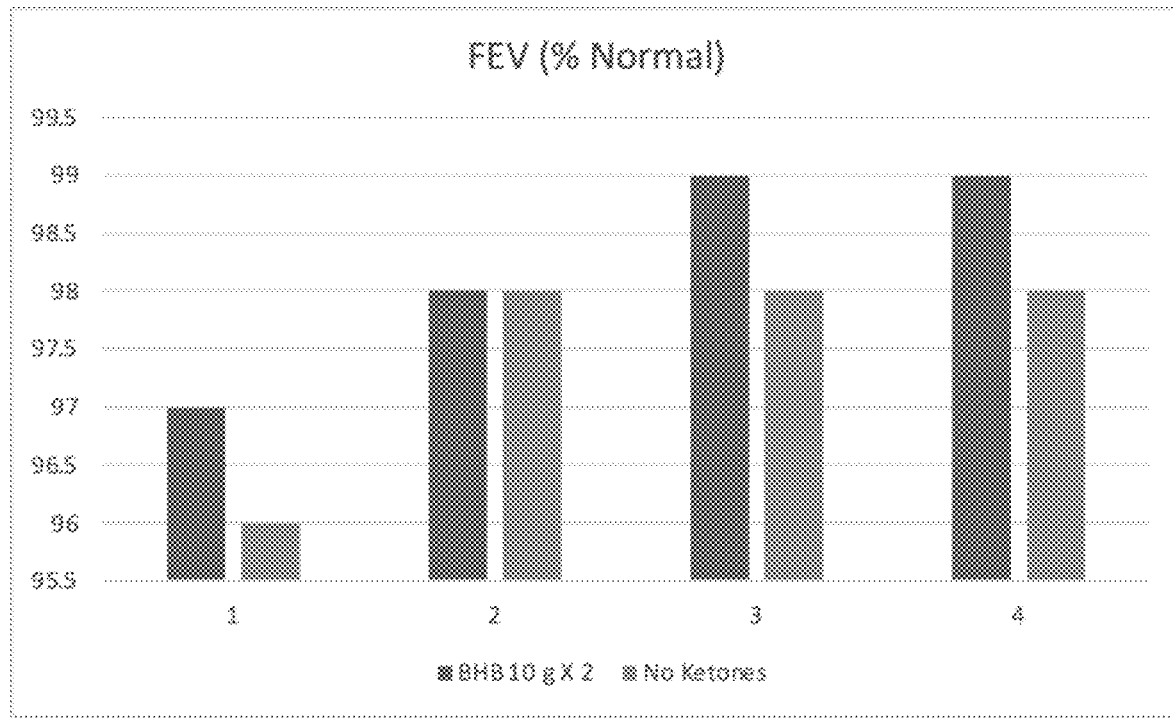
FIG. 2 illustrates a chart of FEV in percentage of normal over time for an implementation of an example administration of beta-hydroxybutyrate in individuals with respiratory illnesses.

FIG. 2 illustrates lung function measurements over 4 days for individuals administered 10 g of R-beta-hydroxybutyrate and not administered 10 g of R-beta-hydroxybutyrate. As illustrated, administration of 10 g of R-beta-hydroxybutyrate kept FEV (as a % of normal FEV) higher overall, indicating improvement in expected decreased lung function due to respiratory illness. Additionally, administration of the beta-hydroxybutyrate caused lung function to improve to normal more quickly. As illustrated, improvement in FEV plateaued when beta-hydroxybutyrate was not administered while it continued to improve when R-beta-hydroxybutyrate was administered. Reduction in the chances of plateauing lung function (e.g., at reduced levels) may decrease potential for long-term continuance of symptoms such as those found in long term or long-haul COVID-19 sufferers (e.g., individuals who had COVID-19 and continue to present with symptoms 4 or more weeks after infection).

Figure 3:
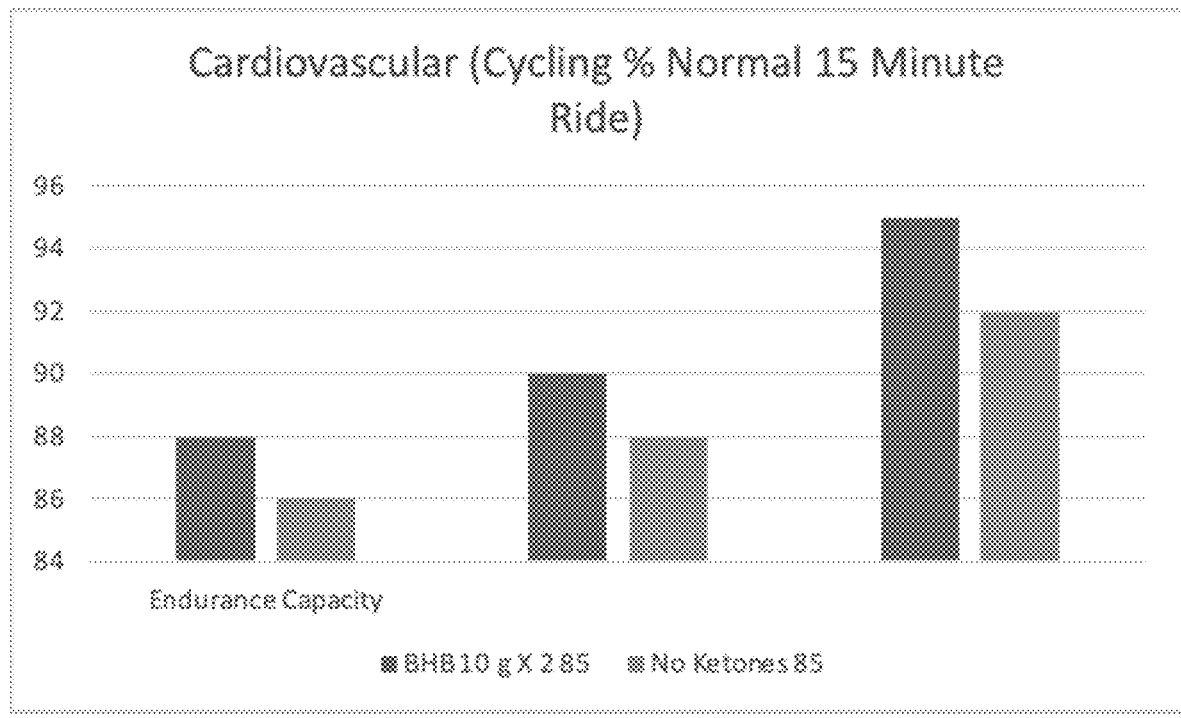
FIG. 3 illustrates a chart of cardiovascular endurance over time for an implementation of an example administration of beta-hydroxybutyrate in individuals with respiratory illnesses.

FIG. 3 illustrates endurance capacity monitoring in individuals over 4 days for individuals administered 10 g of R-beta-hydroxybutyrate and not administered 10 g of R-beta-hydroxybutyrate. Cardiovascular endurance was measured using a standard 15 minute cycling test and is illustrated in FIG. 3 as a percentage of normal. As illustrated, administration the beta-hydroxybutyrate was associated with overall better cardiovascular endurance and quicker recovery to normal cardiovascular endurance.

As illustrated, administration of beta-hydroxybutyrate reduced symptoms, severity of symptoms, and/or recovery times. While the reduction of recovery times, FEV, and/or cardiovascular endurance in coronavirus respiratory illnesses may be associated with reduced hospitalizations and reduced long term prevalence of symptoms.

End of Examples

In various implementations, a composition as described that includes beta-hydroxybutyrate (e.g., R-beta-hydroxybutyrate) may be orally administered to prevent and/or treat respiratory illness(es) and/or symptoms thereof. For example, the composition as described that includes beta-hydroxybutyrate (e.g., R-beta-hydroxybutyrate) may be orally administered to prevent and/or treat coronaviruses, such as COVID-19, and/or symptoms thereof as described herein. In some implementations, a composition as described that includes beta-hydroxybutyrate (e.g., R-beta-hydroxybutyrate) may be orally administered as a daily supplement for the prevention of illness, to reduce symptoms associated with long term symptom(s) of a previous respiratory illness and/or to provide one or more other daily benefits as described herein.

In some implementations, one or more additives may be included in the composition, such as flavorings (e.g., natural and/or artificial), vitamins, minerals, binders, and/or any other appropriate additive. The additives may alter flavor, color, and/or texture. The additives may increase palatability and/or facilitate inclusion in a delivery vehicle (e.g., tablet, food product, beverage product such as a drink mix, etc.). The additive may be any appropriate solid and/or liquid to which the compound is added. For example, an additive may include liquid carriers, such as water, milk(s), and/or any other appropriate drinkable liquid. In some implementations, the composition may include a pharmaceutically inert liquid carrier, such as water (e.g., tap water, filtered water, distilled water, etc.). The liquid carrier may include other drinkable liquids such as coconut water, watermelon water, electrolyte water, and/or combinations thereof. The liquid carrier may include milks such as dairy milk, non-dairy milk, coconut milk, other milks, and/or combinations thereof. The liquid carrier may include an electrolyte solution, in some implementations.

The described compositions may be administered via any appropriate administration method. For example, the described compositions may be administered enterally and/or parenterally. In some implementations, the described composition may be administered via a tablet and/or capsule. The described composition may be provided in a powdered form that allows the described composition to be sprinkled on food, mixed with a liquid to provide a beverage, and/or directly administered. The described composition may be provided in gel form. The compounds in the composition may be mixed, coupled to each other, and/or provided separately. For example, the composition may include beta-hydroxybutyrate coupled to another compound (e.g., beta-hydroxybutyrate ester and/or amino acid). In some implementations, the beta-hydroxybutyrate and one or more other compounds may be provided separately (e.g., in pills). An individual may sequentially and/or concurrently be administered (e.g., swallow pills) the beta-hydroxybutyrate and other compounds.

In some implementations, the compound including beta-hydroxybutyrate may include or may be administered other forms of beta-hydroxybutyrate, butyric acid, and/or butyrate.

Since some compounds included in the described compound (e.g., butyrate, butyric acid, and/or beta-hydroxybutyrate) may not be palatable to some individuals (e.g., since the odor and taste are often compared to vomit), in some implementations, butyrate and/or beta-hydroxybutyrate may be processed to reduce organoleptic reactions. For example, the butyrate and/or beta-hydroxybutyrate (e.g., R-beta-hydroxybutyrate) may be encapsulated, microemulsion, liposomes, agglomeration, masking/flavoring technologies, and/or otherwise processed as appropriate to reduce organoleptic reactions from individuals administered the described composition(s). In some implementations, microencapsulated butyrate, beta-hydroxybutyrate, and/or butyric acid may be utilized (e.g., in combination with beta-hydroxybutyrate). Using microencapsulated butyrate, beta-hydroxybutyrate, and/or butyric acid (e.g., when compared with using unencapsulated forms) may increase individual satisfaction and/or compliance with an administration schedule since odor from the butyrate and/or butyric acid may be reduced and/or removed. The microencapsulated butyrate, beta-hydroxybutyrate, and/or butyric acid may be a free flowing granular powder; dispersible in water; stable in acidic water solution for 30 minutes; allow controlled release in stomach and/or small intestines; inhibit glucose response (e.g., to any added materials); and/or allow delivery of a high butyrate content (e.g., around 70%).

In various implementations, since the described compound is well tolerated by healthy and ill individuals, the described compounds may be used in place of other conventional treatments. In some implementations, since the described compounds are not counter-indicated with conventional respiratory illness medications and treatments, the described compounds may be utilized in conjunction with conventional respiratory illness medications and treatments to reduce the amount and/or frequency of administration of conventional respiratory illness medications.

The described compositions may be administered on an administration protocol to prevent and/or treat respiratory illnesses and/or as a supplement, in some implementations. For example, the described compositions may be administered once a day, via an extended release preparation, and/or multiple times a day (e.g., 1 to 5 times a day, 2 to 5 times a day, 3 to 5 times a day, etc.). For example, the described compounds may be administered, for example, once a day to 5 times a day. As a nonlimiting example, each dosage may be administered as a single capsule and/or tablet, multiple capsules and/or tablets, a powder mixable in liquids and/or food, a beverage, a food item, etc. The described composition may replace other pharmaceuticals or dietary supplements taken and/or be utilized in combination with one or more other pharmaceuticals or dietary supplements, as appropriate to treat illnesses, symptoms thereof and/or to prevent illness.

In various implementations, the described composition(s) (e.g., butyrate, beta-hydroxybutyrate, R-beta-hydroxybutyrate, related compounds, and/or one or more other compounds) may include one or more of the described components, equivalent(s) of the described component(s), derivatives of the described component(s), complex(es) of the described component(s), salt(s) of the described component(s), and/or combinations thereof.

In various implementations, a pharmaceutically effective amount of one or more of the described composition(s) may be administered. Administration of the pharmaceutically effective amount may treat illnesses such as respiratory illnesses (e.g., respiratory illnesses caused by coronaviruses); prevent illnesses such as respiratory illnesses (e.g., respiratory illnesses caused by coronaviruses); improve recovery from illnesses such as respiratory illnesses (e.g., respiratory illnesses caused by coronaviruses); induce and/or maintaining ketosis; maintaining and/or promoting weight loss; increase mental processes (e.g., acuity including cognitive functioning, mood, energy, alertness, focus, performance, effects of aging, etc.); improve and/or maintain body composition; function as a therapeutic for one or more of the described conditions or disorders (e.g., treat neurological disorders); and/or combinations thereof. Although various types of increases in mental acuity have been described, other features of mental acuity such as memory, focus, concentration, and/or understanding (e.g., speed of processing, accuracy of processing) may be increased by administration of an effective amount of the described composition.

Although a subject and/or an individual have been described as a human, a subject and/or individual may be a person or a group of people. Although various described systems and processes have been described as a being administered in humans, the described systems and processes may be administered to other mammals, such as rats, dogs, etc.

In various implementations, beta-hydroxybutyrate may administered simultaneously and/or sequentially with one or more other compounds (e.g., short chain, medium chain, and/or long chain fatty acids). For example, beta-hydroxybutyrate and/or one or more other compounds may be delivered mixed in a powdered, liquid, gel, and/or other appropriate form. In some implementations, the beta-hydroxybutyrate and/or one or more other compounds may be administered via pills, tablets, capsules, other oral administration forms, intravenously, nasal sprays, sublingual tabs/strips, or topical delivery, rectal, other appropriate administration forms, and/or combinations thereof.

Although the term beta-hydroxybutyrate is the terminology used in the described implementations, beta-hydroxybutyrate is also referred to as beta-hydroxybutyrate, (R)-3-Hydroxybutyric acid, (R)-3-Hydroxybutanoic acid, (3R)-3-hydroxybutanoic acid, (R)-3-Hydroxybutanoate, (R)-(−)-3-Hydroxybutyric acid, (R)-(−)-beta-Hydroxybutyric acid, 3-D-hydroxybutyrate, BHIB, BHB, 3-delta-hydroxybutyrate, delta-3-hydroxybutyrate, 3-D-hydroxybutyric acid, D-3-hydroxybutyric acid, 3R-hydroxy-butanoic acid, delta-beta-hydroxybutyrate, D-3-hydroxybutyrate, D-(−)-3-hydroxybutyrate, delta-3-hydroxybutyric acid, (−)-3-Hydroxybutyric acid, D-beta-hydroxybutyrate, (R)-(−)-b-Hydroxybutyrate, (R)-beta-Hydroxybutyric acid, delta-(−)-3-hydroxybutyrate, (R)-3-hydroxybutyrate, (R)-beta-Hydroxybutanoic acid, (R)-(−)-beta-hydroxybutyrate, (−)-3-Hydroxy-n-butyric acid, (R)-(−)-b-Hydroxybutyric acid, Butanoic acid, 3-hydroxy-, (R)-Butyric acid, 3-hydroxy-, D-(−)-(R)-3-82578-46-9, beta-D-Hydroxybutyric acid, D-beta-Hydroxybutyric acid, (3R)-3-delta-hydroxybutyric acid, 3-(R)-Hydroxybutyric acid, and/or (−)-beta-Hydroxybutyrate.

In various implementations, beta-hydroxybutyrate is described as included in a composition; administered in an amount, form, and/or schedule; and/or being in a particular form (e.g., complexed and/or coupled). R-beta-hydroxybutyrate may be utilized in the various described implementations of beta-hydroxybutyrate in the same or lower amount as the described beta-hydroxybutyrate, as appropriate.

References to an amount (e.g., weight) of beta-hydroxybutyrate refers to the quantity of beta-hydroxybutyrate in a compound rather than the total amount (e.g., total weight) of the compound. For example, when 10 g of a beta-hydroxybutyrate is administered as sodium beta-hydroxybutyrate salt, the total amount of sodium beta-hydroxybutyrate is approximately 12.2 g (2.2 g sodium and 10 g beta-hydroxybutyrate).

The disclosure of U.S. patent application Ser. No. 15/491,924, entitled "ADMINISTRATION OF BUTYRATE, BETA-HYDROXYBUTYRATE, AND RELATED COMPOUNDS IN HUMANS", filed on Apr. 19, 2017, is incorporated by reference for all purposes to the extent that its disclosure does not conflict with the disclosure herein.

It is to be understood the implementations are not limited to particular systems or processes described which may, of course, vary. It is also to be understood that the terminology used herein is for the purpose of describing particular implementations only, and is not intended to be limiting. As used in this specification, the singular forms "a", "an" and "the" include plural referents unless the content clearly indicates otherwise. Thus, for example, reference to "a compound" includes a combination of two or more compounds and reference to "a beta-hydroxybutyrate" includes different types and/or combinations of beta-hydroxybutyrate.

Although the present disclosure has been described in detail, it should be understood that various changes, substitutions and alterations may be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A method of improving one or more respiratory illnesses in an individual, the method comprising:
orally administering, to an individual, a pharmaceutically effective amount of a composition comprising:
approximately 0.5 g to approximately 10 g of R-beta-hydroxybutyrate, wherein the R-beta-hydroxybutyrate comprises at least one R-beta-hydroxybutyrate salt; and
wherein the administration of the composition improves respiratory illnesses in an individual.

2. The method of claim 1 wherein the composition comprises less than approximately 2 g of R-beta-hydroxybutyrate.

3. The method of claim 1 wherein the approximately 0.5 g to approximately 10 g of R-beta-hydroxybutyrate comprises at least approximately 90% R-beta-hydroxybutyrate and less than approximately 10% L-beta-hydroxybutyrate.

4. The method of claim 1 wherein the R-beta-hydroxybutyrate comprises at least one a beta-hydroxybutyrate salt and at least one beta-hydroxybutyrate polymer.

5. The method of claim 1 wherein the 0.5 to 10 g of R-beta-hydroxybutyrate comprises an R-beta-hydroxybutyrate-complex.

6. The method of claim 1 the composition may include at least one additional compound, and wherein at least one of the additional compounds comprises:
a short chain fatty acid,
an ester of short chain fatty acid;
a medium chain fatty acid,
an ester of medium chain fatty acid;
a long chain fatty acid,
or an ester of long chain fatty acid.

7. The method of claim 1 wherein the composition further comprises approximately 1 g to approximately 20 g of at least one of one or more medium chain fatty acids or one or more medium chain fatty acid esters.

8. The method of claim 1 wherein the composition further comprising a C8 fatty acid.

9. The method of claim 1 wherein the composition comprises at least one of a flavoring, a vitamin, a mineral, or liquid carrier.

10. The method of claim 1 wherein the composition further comprises at least one amino acid.

11. The method of claim 1 wherein administering the pharmaceutically effective amount of the R-beta-hydroxybutyrate increases strength and mental acuity in the individual with the at least one respiratory illness.

12. The method of claim 1 wherein at least one of the respiratory illnesses comprises COVID-19.

13. The method of claim 1 wherein at least one of the respiratory illnesses comprises COVID-19, and wherein administration of the pharmaceutically effective amount of the R-beta-hydroxybutyrate reduces or inhibits long term symptoms of COVID-19 related to decreased lung function as determined by forced expiratory volume (FEV).

14. The method of claim 1 wherein administration of the composition decreases at least one of the number of symptoms or the severity of the symptoms of the at least one respiratory illness.

15. A method of improving lung function in an individual with a respiratory illness, the method comprising:
orally administering, to an individual, a pharmaceutically effective amount of a composition comprising beta-hydroxybutyrate, wherein the beta-hydroxybutyrate comprises:
approximately 0.5 g to approximately 15 g of one or more beta-hydroxybutyrate salts; and
wherein the administration of the composition improves lung function in an individual with at least one respiratory illness.

16. The method of claim 15 wherein the composition comprises less than approximately 2 g of beta-hydroxybutyrate.

17. The method of claim 15 wherein the approximately 0.5 g to approximately 10 g of beta-hydroxybutyrate comprises at least approximately 90% R-beta-hydroxybutyrate and less than approximately 10% L-beta-hydroxybutyrate.

18. A method of improving one or more respiratory illnesses in an individual, the method comprising:

orally administering, to an individual, a pharmaceutically effective amount of a composition comprising beta-hydroxybutyrate, wherein the beta-hydroxybutyrate comprises:

approximately 0.5 g to approximately 10 g of one or more beta-hydroxybutyrate salts; and wherein the administration of the composition improves respiratory illnesses in an individual.

19. The method of claim 18 wherein the composition further comprises at least one beta-hydroxybutyrate polymer.

20. The method of claim 18 wherein the composition further comprises at least one amino acid.

* * * * *